United States Patent [19]

Szente

[11] 4,046,890
[45] Sept. 6, 1977

[54] BENZODIAZEPINE DERIVATIVES

[75] Inventor: Andre Szente, Basel, Switzerland

[73] Assignee: Hoffmann-La Roche Inc., Nutley, N.J.

[21] Appl. No.: 589,495

[22] Filed: June 23, 1975

[30] Foreign Application Priority Data

June 28, 1974 Switzerland .......... 8926/74

[51] Int. Cl.² .......... C07D 243/24
[52] U.S. Cl. .......... 424/244; 260/239.3 D; 260/562 N; 260/562 B; 260/570 AB
[58] Field of Search .......... 260/239.3 D; 424/244

[56] References Cited

U.S. PATENT DOCUMENTS

| | | | |
|---|---|---|---|
| 3,116,203 | 12/1963 | Kariss et al. | 260/239.3 D |
| 3,121,076 | 2/1964 | Keller et al. | 260/239.3 D |
| 3,123,529 | 3/1964 | Kariss et al. | 260/239.3 D |
| 3,248,223 | 4/1966 | Bauernfeind | 260/239.3 D |
| 3,998,811 | 12/1976 | Kajfez et al. | 260/239.3 D |

FOREIGN PATENT DOCUMENTS 6,500,446  7/1965  Netherlands .......... 260/239.3 D

OTHER PUBLICATIONS

Sunjic et al., "J. Het. Chem." vol. 10 (1973) pp. 591–599.
Stempel et al., "J. Org. Chem." vol. 27 (1962) pp. 4675–4677.

Primary Examiner—Henry R. Jiles
Assistant Examiner—Robert T. Bond
Attorney, Agent, or Firm—Samuel L. Welt; Bernard S. Leon; Frank P. Hoffman

[57] ABSTRACT

This invention is directed to pharmacologically active compounds of the formula

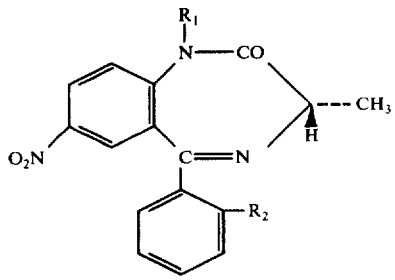

wherein $R_1$ represents a hydrogen atom or lower alkyl group and $R_2$ represents a halogen atom.

The compounds of formula I are optically active and have the absolute configuration S at the carbon atom in the 3-position. They exhibit anthelmintic, sedative, anticonvulsant and muscle relaxant activity.

Also provided are methods for their preparation and formulations which incorporate the active compounds.

6 Claims, No Drawings

BENZODIAZEPINE DERIVATIVES

DESCRIPTION OF THE INVENTION

The present invention relates to benzodiazepine derivatives. More particularly, the invention is concerned with benzodiazepine derivatives, a process for the manufacture thereof and pharmaceutical preparations containing same.

The benzodiazepine derivatives provided by the present invention are optically active 1,4-benzodiazepine-2-ones of the general formula

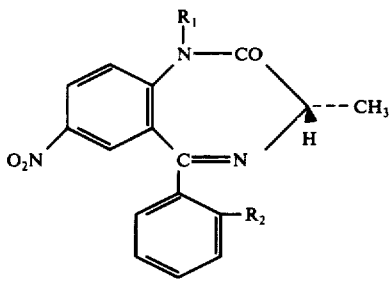

I

, wherein $R_1$ represents a hydrogen atom or a lower alkyl group and $R_2$ represents a halogen atom, which have the absolute configuration S at the carbon atom in the 3-position.

As used in this specification, the term "lower alkyl" denotes a straight-chain or branched-chain, saturated, aliphatic hydrocarbon group containing up to 5 carbon atoms such as the methyl, ethyl, propyl, isopropyl groups and the like. The methyl group is the preferred lower alkyl group. The term "halogen" denotes chlorine, bromine, iodine and fluorine.

In a preferred embodiment of the present invention, $R_1$ represents a hydrogen atom or the methyl group. $R_2$ preferably represents a chlorine atom.

According to the process provided by the present invention, the optically active 1,4-benzodiazepin-2-ones of formula I hereinbefore are manufactured by a. cyclizing a compound of the general formula

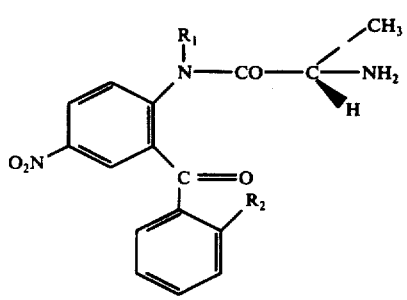

II

, wherein $R_1$ and $R_2$ have the significance given earlier, or b. reacting a compound of the general formula

III

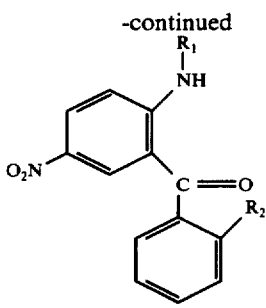

, wherein $R_1$ and $R_2$ have the significance given earlier, with L-alanine or a reactive functional derivative thereof, or c. for the manufacture of an optically active 1,4-benzodiazepin-2-one of formula I in which $R_1$ represents a lower alkyl group, lower alkylating an optically active 1-unsubstituted -1,4-benzodiazepin-2-one of the general formula

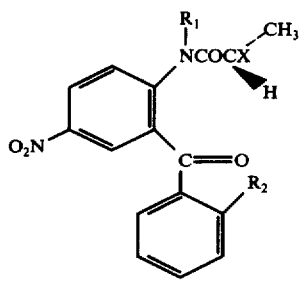

IA wherein $R_2$ has the significance given earlier.

According to embodiment (a) of the foregoing process, an optically active 1,4-benzodiazepin-2-one of formula I is manufactured by cyclizing a compound of formula II which, in turn, can be prepared from a corresponding compound of the general formula

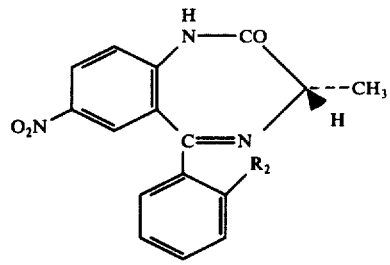

IV wherein $R_1$ and $R_2$ have the significance given earlier and X represents a carbobenzoxyamino group or a phthalimido group.

A compound of formula II which is initially obtained from a compound of formula IV is preferably not isolated, but is cyclized in situ under the reaction conditions used and is accordingly converted directly into a desired optically active 1,4-benzodiazepin-2-one of formula I. On the other hand, a compound of formula II can be isolated and then subsequently subjected to a ring-closure to give a desired optically active 1,4-benzodiazepin-2-one of formula I. The cyclization is expediently carried out by slightly heating a compound of formula II, which is preferably dispersed in an inert organic solvent.

Where a compound of formula IV in which X represents a carbobenzoxyamino group is used, the cyclization is carried out by first removing the amino protecting group, for example, by treatment with hydrogen bromide in glacial acetic acid, a salt of a compound of formula II being obtained. This salt is then cyclized to an optically active 1,4-benzodiazepin-2-one of formula I by making the reaction mixture alkaline. This reaction is expediently carried out in the presence of an inert organic solvent such as dimethyl sulphoxide, dimethylformamide, hexametapol, a lower alkanol (e.g. methanol, ethanol and the like), and ether (e.g. diethyl ether, tetrahydrofuran, ethylene glycol dimethyl ether and the like), a chlorinated hydrocarbon (e.g. methylene chloride and the like) or pyridine.

Where a compound of formula IV in which X represents a phthalimido group is used, the cyclization is carried out by treating said compound with hydrazine hydrate. This treatment is perferably carried out in the presence of an inert organic solvent.

According to embodiment b) of the foregoing process, the optically active 1,4-benzodiazepin-2-ones of formula I are manufactured by reacting a compound of formula III under weak acidic conditions with L-alanine or a reactive functional derivative thereof, especially an ester thereof (preferably the methyl or ethyl ester).

In a preferred aspect of embodiment b), a compound of formula III is reacted with a lower alkyl ester of L-alanine under weak acidic conditions.

In carrying out the aforementioned reaction between a compound of formula III and an L-alanine ester, the ester is preferably used in the form of its hydrochloride. This reaction is expediently carried out in the presence of inert organic solvents such as alcohols having a chain of at least 3 carbon atoms (e.g. propanol, butanol and the like) or aromatic hydrocarbons (e.g. benzene, toluene, xylene and the like). Of the acids with which the reaction mixture is expediently made slightly acidic, there may be mentioned pivalic acid and p-toluenesulphonic acid. The reaction is preferably carried out at an elevated temperature, especially at the reflux temperature of the reaction mixture.

Optically active 1,4-benzodiazepin-2-ones of formula I in which $R_1$ represents a hydrogen atom can be converted into corresponding optically active 1,4-benzodiazepin-2-ones of formula I in which $R_1$ represents a lower alkyl group according to embodiment c) of the foregoing process using methods known per se. For example, an optically active 1,4-benzodiazepin-2-one of formula I in which $R_1$ represents a hydrogen atom can first be converted into a 1-sodio derivative using sodium methoxide, sodium hydride or the like and the resulting 1-sodio derivative can then be lower alkylated using customary lower alkylating agents such as methyl iodide, ethyl iodide, dimethyl sulphate and the like. The lower alkylation is expediently carried out in the presence of any customary inert organic solvent system, one or more inert organic solvents such as acetone, dimethyl sulphoxide, dimethylformamide, hexametapol, benzene, toluene and N-methylpyrrolidine or the like being used.

The compounds of formula IV can be prepared in a manner known per se from the compounds of formula III; for example, by reacting a compound of formula III with a reactive derivative (e.g. the acid chloride) of carbobenzoxy-L-alanine or phthalimido-L-alanine.

The compounds of formula III are known and can be prepared in a manner known per se.

In carrying out the process provided by the present invention, the reaction conditions are always chosen so that substantially no racemisation can occur.

The optically active 1,4-benzodiazepin-2-ones of formula I are useful as medicaments. They possess an extremely pronounced anthelmintic, especially schistosmicidal, activity and, in addition, exhibit the muscle relaxant, anticonvulsant and sedative activity which is common in benzodiazepines. Surprisingly, it has been shown that the corresponding antipodes having the absolute configuration R as well as the corresponding racemates exhibit no anthelmintic activity and respectively only slight anthelmintic activity. The optically active 1,4-benzodiazepin-2-ones of formula I can be used, for example, for the therapy of bilharzia. The following test is given by way of example of demonstrate the schistosomicidal activity of the optically active 1,4-benzodiazepin-2-ones of formula I.

Mice or golden hamsters are infected subcutaneously with 60 cercaria of Schistosoma mansoni. Approximately 42 days after the infection, the animals are treated with the substances to be tested on 5 successive days. 5–10 animals are used per substance and dosage (mg/kg). 10 untreated animals are used as controls. The section is carried out 6 days or 2–3 weeks after termination of the treatment. Worm pairs in the mesenteric veins, portal vein and liver are dissected out and counted. The percentage distribution of the worm pairs in the mesenteric veins, portal vein and liver is calculated and the condition of the worms (living, dead) registered. The activity of the test substance is shown in an increased proportion of the worms in the vessels of the liver and in the appearance of dead worms.

For evaluation, the percentage proportion of living and dead worm pairs in the vessels of the liver is compared not only in the infected treated animals but also in the infected, but untreated, control animals. The determination of the $SD_{50}$ (Shift Dose 50%: dose which dispels 50% of the worm pairs into the liver in a group of treated animals) and $VD_{50}$ (Vermicidal Dose 50%: dose which kills 50% of the worm pairs) is carried out according to the probit analysis.

Some test results are compiled in the following table:

Table

| Test substance | $SD_{50}$ mg/kg mouse/hamster | $VD_{50}$ mg/kg mouse/hamster |
| --- | --- | --- |
| (+)-5-(o-chlorophenyl)-1,3-dihydro-3-methyl-7-nitro-2H-1,4-benzodiazepin-2-one | 27/52 | 28/47 |
| (+)-5-(o-chlorophenyl)-1,3-dihydro-1,3-dimethyl-7-nitro-2H-1,4-benzodiazepin-2-one | 52/85 | 58/95 |

The optically active 1,4-benzodiazepin-2-ones of formula I can be used as medicaments; for example, in the form of pharmaceutical preparations which contain them in association with a compatible pharmaceutical carrier. This carrier can be an organic or inorganic carrier material suitable for enteral or parenteral administration such as gelatine, lactose, starch, gum arabic, magnesium stearate, talcum, vegetable oils, polyalkyleneglycols, petroleum jelly and the like. The pharmaceutical preparations can be made up in a solid form (e.g. as tablets or dragees) or in a liquid form (e.g. as solutions, suspensions or emulsions). They can contain adjuvants such as preservatives, stabilizers, wetting agents, emulsifiers, salts for varying the osmotic pressure or buffers. The pharmaceutical preparations can contain additional therapeutically active substances.

Expedient pharmaceutical dosage forms contain 5–50 mg, preferably about 5 mg, of an optically active 1,4-benzodiazepin-2-one of formula I.

The dosage is selected according to the individual requirements. For example, the present optically active 1,4-benzodiazepin-2-ones can be administered in dosages of from about 0.1 mg/kg to about 10 mg/kg per day p.o., preferably 0.3 mg/kg per day p.o. This amount can be administered in a single dosage or in several subdivided dosages according to the needs of the patient and the instructions of the attending physician. This dosage is expediently administered, having regard to the condition of the patient, on several successive days, preferably on 5 to 8 successive days.

The following Examples illustrate the process provided by the present invention.

EXAMPLE 1

82 g of carbobenzoxy-L-alanine are dissolved in 100 ml of absolute tetrahydrofuran, the solution is cooled to −40° C and treated with 80 g of phosphorus pentachloride. The reaction mixture is stirred at −30° C for 20 minutes and subsequently added to a shaken solution of 80 g of 2-amino-5-nitro-2'-chlorobenzophenone in 100 ml of absolute tetrahydrofuran. The solution is concentrated on a rotary evaporator at 50°–60° C, treated twice with toluene and evaporated each time. By crystallization of the residue from ether, there is obtained (−)-benzyl-[1-[{2- (ochlorobenzoyl)-4-nitrophenyl}-carbamoyl]-ethyl]carbamate which melts at 147° C and exhibits a rotation of $[\alpha]_{25}^D = -18.2°$ (in methylene chloride, 1%).

9.2 g of the foregoing carbamate are stirred in 90 ml of a 30% solution of hydrogen bromide in glacial acetic acid for 2 hours at room temperature and then the mixture is concentrated on a rotary evaporator. The residue is dissolved in water, the aqueous solution washed three times with ether and then made alkaline with sodium bicarbonate. The precipitated product is extracted with methylene chloride, the methylene chloride, the methylene chloride phase dried over sodium sulphate and concentrated. The residue is crystallized from ether and recrystallized from methylene chloride/petroleum ether, there being obtained (+)-2-amino-2'-(o-chlorobenzoyl)-4'-nitropropionoanilide which melts at 132° C and exhibits a rotation of $[\alpha]_{25}^D = +4.4°$ (in methylene chloride, 2%). 35 g of foregoing propionoanilide are heated to reflux in 40 ml of glacial acetic acid and 200 ml of absolute toluene for 15 minutes. The residue obtained after distillation of the solvent is treated with methylene chloride and 10% sodium bicarbonate solution. The methylene chloride solution is washed twice with 10% sodium bicarbonate solution and once with water, dried over sodium sulphate, filtered and concentrated. The residue is taken up in benzene, some racemate formed crystallizing out and being filtered off. The benzene solution is evaporated and the residue crystallized from ether to give (+)-5-(o-chlorophenyl)-1,3-dihydro-3-methyl-7-nitro-2H-1,4-benzodiazepin-2-one which melts at 198°–200° C and exhibits a rotation of $[\alpha]_{25}^D = +252.1°$ (in methylene chloride, 1%).

EXAMPLE 2

10 g of (+)-5-(o-chlorophenyl)-1,3-dihydro-3-methyl-7-nitro-2H-1,4-benzodiazepin-2-one are dissolved in 100 ml of acetone and treated with 6.3 g of potassium carbonate and 3.5 ml of dimethyl sulphate. After stirring for 2 hours at room temperature, a further 1 g of potassium carbonate and 1 ml of dimethyl sulphate are added, after which the mixture is stirred for a further hour at room temperature. The mixture is treated with 3 ml of glacial acetic acid and the acetone is distilled off. The residue is treated with 10% sodium bicarbonate solution and extracted with methylene chloride. The methylene chloride solution is dried over sodium sulphate, filtered and concentrated. The residue is purified on a column of silica gel (eluant: methylene chloride and methylene chloride/ethyl acetate 10:1) and crystallized from ether/ petroleum ether. There is obtained (+)-5-(o-chlorophenyl)--1,3-dihydro-1,3-dimethyl-7-nitro-2H-1,4-benzodiazepin-2-one which melts at 156°–158° C and exhibits a rotation of $[\alpha]_{25}^D = +376.2°$ (in methylene chloride, 1%).

The following Examples illustrate typical pharmaceutical preparations containing the optically active 1,4-benzodiazepin-2-ones of formula I as the active ingredient:

EXAMPLE A

Tablets of the following composition are manufactured:

| | |
|---|---|
| Active ingredient of formula I | 5.0 mg |
| Lactose | 100.0 mg |
| Maize starch | 85.0 mg |
| Ethylcellulose | 10.0 mg |
| Talcum | 4.5 mg |
| Magnesium stearate | 0.5 mg |
| | 205.0 mg |

The active ingredient is mixed with the lactose and the maize starch and granulated with a solution of the ethylcellulose in 40 ml of methylene chloride. The granulate is dried at 40° C, mixed with the talcum and magnesium stearate and pressed to tablets.

| | |
|---|---|
| Weight of one tablet | 205 mg |
| Active ingredient content of one tablet | 5 mg |

EXAMPLE B

Capsules containing the following ingredients are manufactured:

| | |
|---|---|
| Active ingredient of formula I | 5.0 mg |
| Lactose | 155.0 mg |
| Maize starch | 30.0 mg |
| Talcum | 15.0 mg |
| | 205.0 mg |

The active ingredient is homogeneously mixed with the lactose and the maize starch, passed through a sieving machine and, after intermixing of the talcum, filled into gelatine capsules.

| | |
|---|---|
| Fill-weight of capsule | 205 mg |
| Active ingredient content | 5 mg |

I claim:

1. An optically active 1,4-benzodiazepin-2-one of the general formula

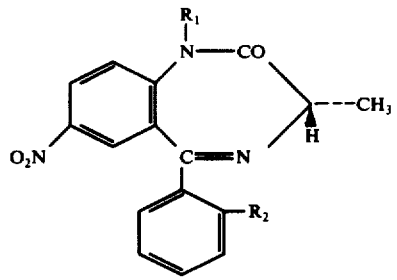

wherein $R_1$ represents a hydrogen atom or a lower alkyl group and $R_2$ represents a halogen atom, which have the absolute configuration S at the carbon atom in the 3-position.

2. An optically active 1,4-benzodiazepin-2-one according to claim 1, wherein $R_1$ represents a hydrogen atom or the methyl group and $R_2$ represents a chlorine atom.

3. A compound of the formula: (+)-5-(o-chlorophenyl)-1,3-dihydro-3-methyl-7-nitro-2H-1,4-benzodiazepin-2-one.

4. A compound of the formula: (+)-5-(o-chlorophenyl)-1,3-dihydro-1,3-dimethyl-7-nitro-2H-1,4-benzodiazepin-2-one.

5. An anthelmintic composition which comprises an anthelmintically active amount of a compound of the formula

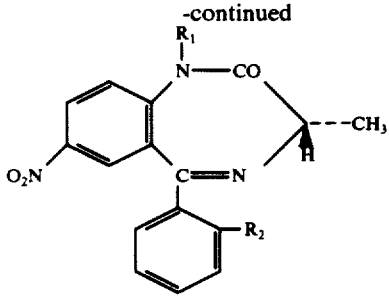

wherein $R_1$ represents a hydrogen atom or a lower alkyl group and $R_2$ represents a halogen atom, which has the absolute configuration S at the carbon atom in the 3-position and a nontoxic, inert, therapeutically compatible carrier.

6. A method of treating schistosomicides comprising the administration of schistosomicidally active amounts of a compound of the formula

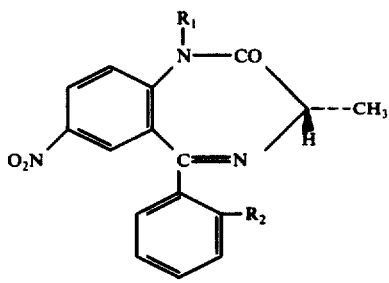

wherein $R_1$ represents a hydrogen atom or a lower alkyl group and $R_2$ represents a halogen atom, which has the absolute configuration S at the carbon atom in the 3-position in association with a nontoxic, inert, therapeutically compatible carrier.

* * * * *